Figure 1A:
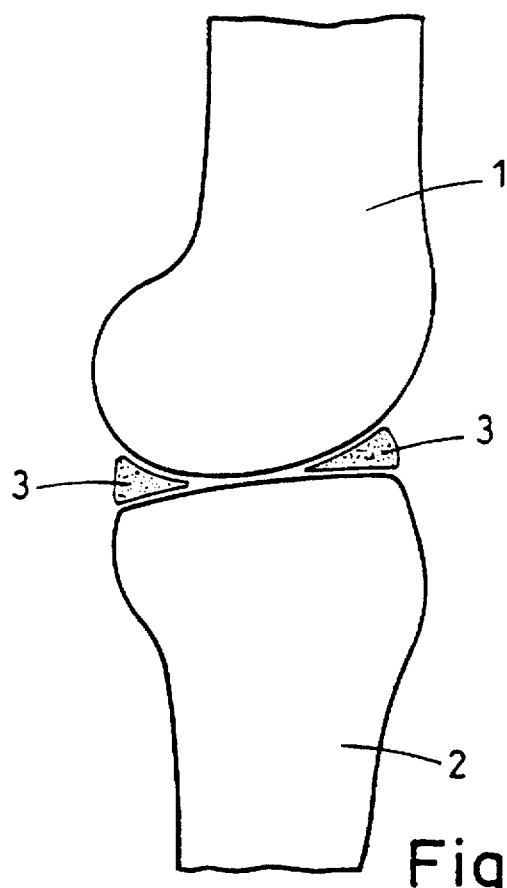

United States Patent
Walker et al.

[11] Patent Number: 5,725,584
[45] Date of Patent: Mar. 10, 1998

[54] KNEE PROSTHESIS WITH FEMORAL, TIBIAL CONFORMITY

[76] Inventors: Peter Stanley Walker, 13 Pembroke Road, Moor Park, Middlesex, England, HA8 2HP; John Nevil Insall, 170 East End Ave., New York, N.Y. 10128

[21] Appl. No.: 638,085

[22] Filed: Apr. 26, 1996

Related U.S. Application Data

[63] Continuation of Ser. No. 373,323, filed as PCT/GB94/01047, May 17, 1994, published as WO94/26212, Nov. 24, 1994, abandoned.

[30] Foreign Application Priority Data

May 18, 1993 [GB] United Kingdom ............... 9310193

[51] Int. Cl.⁶ ........................................................ A61F 2/38
[52] U.S. Cl. ........................................................... 623/20
[58] Field of Search ................................. 623/16, 18, 20

[56] References Cited

U.S. PATENT DOCUMENTS

| | | |
|---|---|---|
| 4,285,070 | 8/1981 | Averill. |
| 4,340,978 | 7/1982 | Buechel et al. |
| 4,959,071 | 9/1990 | Brown et al. ............... 623/20 |
| 5,064,437 | 11/1991 | Stock et al. ............... 623/20 |
| 5,071,438 | 12/1991 | Jones et al. |
| 5,171,283 | 12/1992 | Pappas et al. |
| 5,282,868 | 2/1994 | Bahler ....................... 623/20 |
| 5,358,527 | 10/1994 | Forte ......................... 623/20 |
| 5,370,700 | 12/1994 | Sarkisian et al. ......... 623/20 |

FOREIGN PATENT DOCUMENTS

| | | |
|---|---|---|
| 0 327 297 | 8/1989 | European Pat. Off. |
| 0 498 586 | 8/1992 | European Pat. Off. |
| 2 219 942 | 6/1988 | United Kingdom. |
| 92 03108 | 3/1992 | WIPO. |

*Primary Examiner*—David Isabella
*Attorney, Agent, or Firm*—Lowe, Price, LeBlanc & Becker

[57] ABSTRACT

A femoral prosthesis is disclosed comprising a bicondylar femoral component (41), a tibial component (72) and at least one meniscal component (42) interposed between the femoral and tibial components, the femoral component including a pair of condylar surfaces (46) separated by a patella bearing surface (44) which in use provides a normal anatomical patella lever arm, the condylar surfaces being shaped for substantial conformity with corresponding tibial bearing surfaces (47) of the meniscal component or components over the entire range of normal flexion.

7 Claims, 5 Drawing Sheets

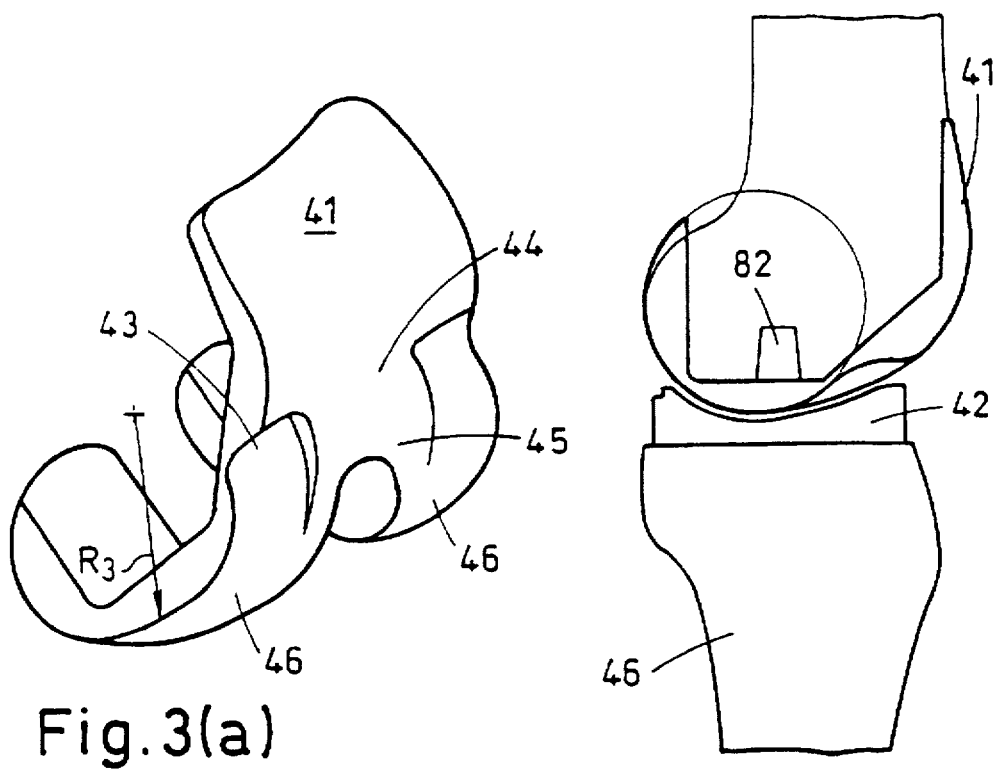
Fig. 3(a)
Fig. 3(c)
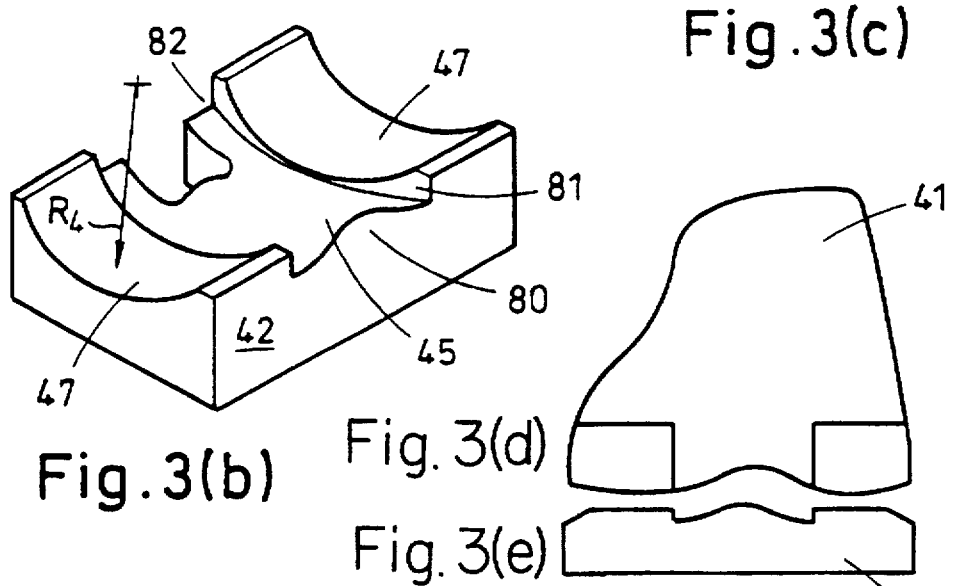
Fig. 3(b)
Fig. 3(d)
Fig. 3(e)
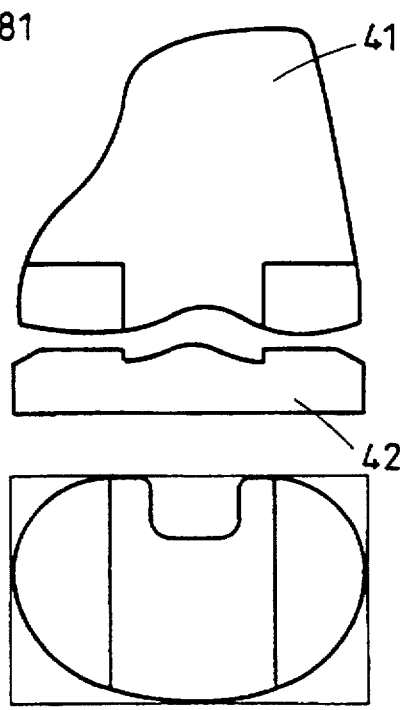
Fig. 3(f)

KNEE PROSTHESIS WITH FEMORAL, TIBIAL CONFORMITY

This application is a continuation of application Ser. No. 08/373,323, filed as PCT/GB94/01047 on May 17, 1994 published as WO94/26212 filed on Nov. 24, 1994 now abandoned.

This invention relates to a prosthesis for knee replacement. In the replacement of diseased or deformed knee joints, the arthritic or otherwise damaged joint surfaces are resected and replaced with artificial metal and plastic surfaces. Current designs have centred on a prosthesis having three components, i.e. a femoral component designed to replace the condylar surfaces of the natural knee joint and having provision for guidance of the natural or a replacement patella, a tibial component which includes a generally horizontal support plate fixed to the resected tibia and a meniscal component, normally of plastics material, which is attached to the tibial component and is shaped to provide a bearing surface for the condylar portions of the femoral component.

Existing commercial designs have provided for some degree of laxity between the femoral component and the meniscal component in order to allow for limited freedom of motion within the artificial joint in use. This is necessary in order to mimic to some extent the natural motion of the joint which includes rotation in a horizontal plane as well as some forward and backward relative motion during flexion.

One disadvantage of permitting some laxity between the bearing surfaces of the femoral component and the tibial component is that this results in high contact pressures and stresses on bearing surfaces, since laxity is conventionally achieved by providing a low degree of conformity between the mutually bearing surfaces.

It is a primary object of the present invention to provide a knee prosthesis which includes a high degree of femoral, tibial conformity but at the same time, is capable of permitting some degree of anterior-posterior motion and rotational motion during flexion.

According to one aspect of the present invention there is provided a prosthesis which comprises a bicondylar femoral component, a tibial component and a meniscal component interposed between the femoral and tibial components, the femoral component including a pair of condylar surfaces separated by a patella bearing surface which in use provides a normal anatomical patella lever arm, the condylar surfaces being shaped for substantially close conformity with corresponding surfaces of the meniscal component or components in flexion over the entire range of normal flexion. By the entire range of normal flexion we mean 0° to about 120°, preferably to about 130° or 135°.

Figure 2A:
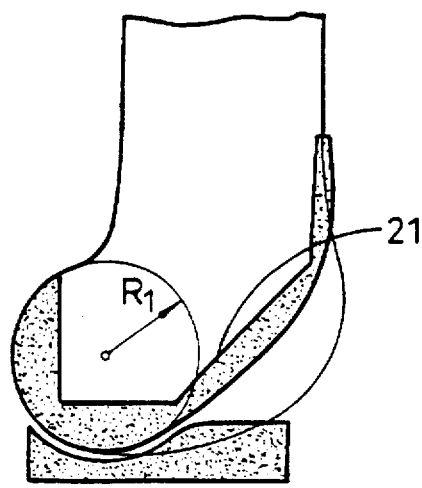
Figure 4A:
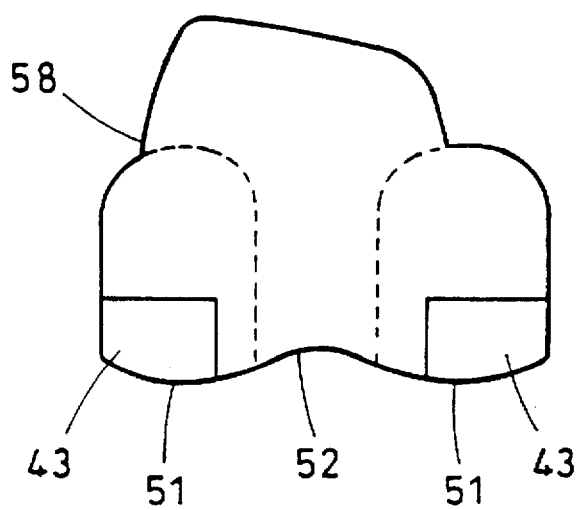
Figure 4B:
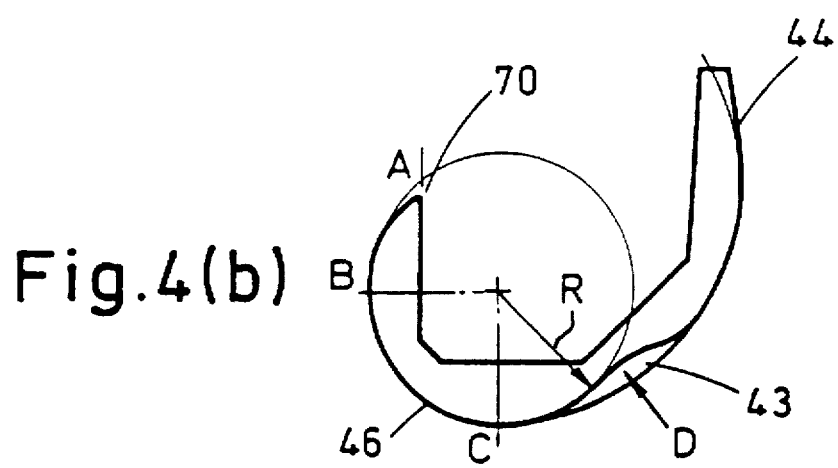
Figure 4C:
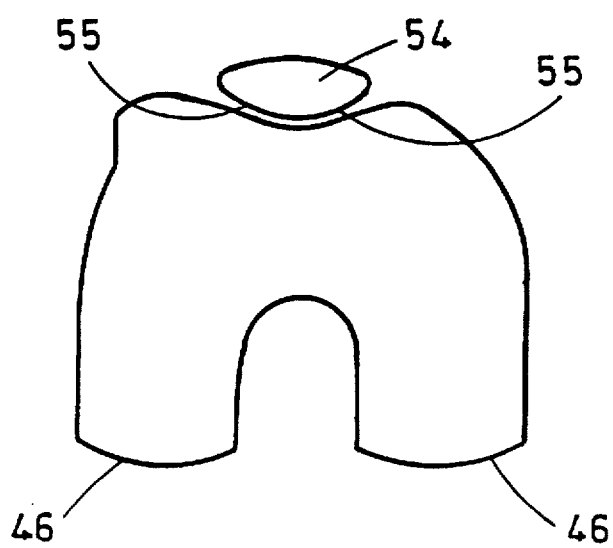
Figure 5:
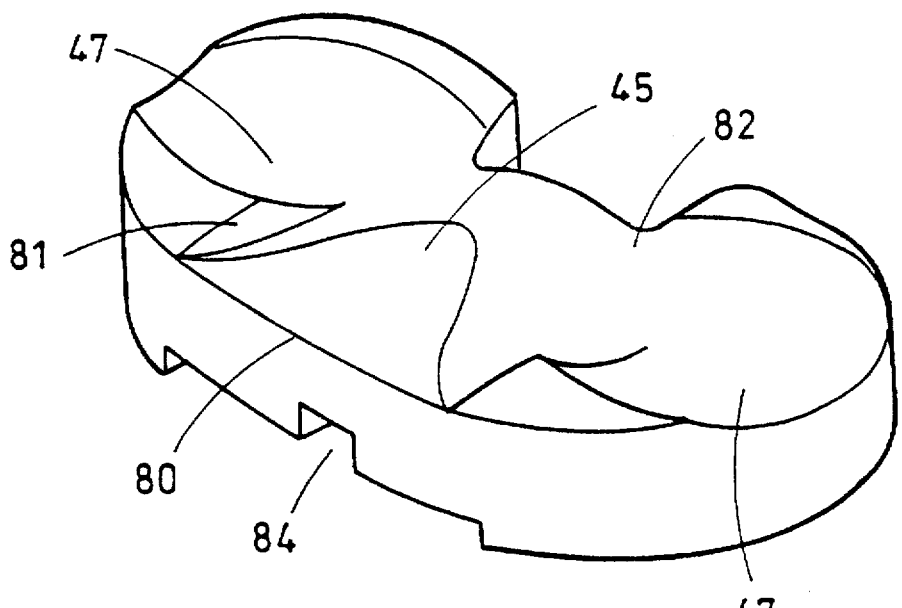
Figure 6:
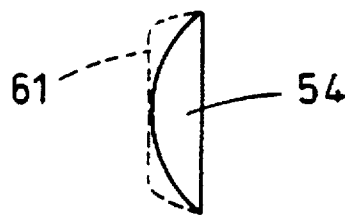
Figure 7:
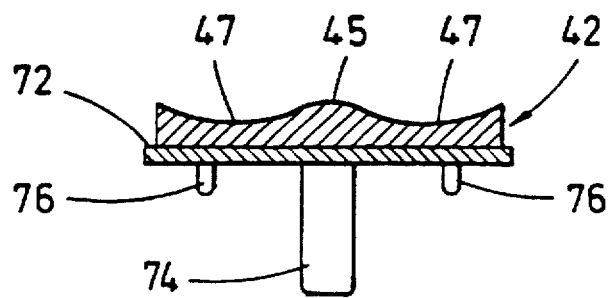

Further features and advantages of the present invention will become apparent from the accompanying drawings, in which:

FIGS. 1(a), (b), (c) and (d) illustrate prior art approaches to the problem of providing a prosthesis mimicking the movement of a natural joint, FIGS. 2(a), (b) and (c) illustrate approaches to the solutions to the problems presented in the prior art, FIGS. 3(a), (b), (c) and (d), (e) and (f) show various diagrammatic views of one embodiment in accordance with the invention, FIGS. 4(a), 4(b) and 4(c) show three views of the embodiment of FIGS. 3(a) to (3(d) in more detail, FIG. 5 is a perspective view of a meniscal component of the prosthesis in accordance with the invention, FIG. 6 is a sagittal view of the profile of a plastics patella of preferred shape (in broken lines) with a conventional artificial patella shown in full lines, and FIG. 7 is a lateral-medial section through the meniscal component and tibial base plate.

Referring to FIGS. 1, 1(a) shows a section through a natural knee joint from which one can see that there is a lack of congruity between the femoral condyles (1) and the tibia (2). In the natural knee, menisci (3) which are formed from cartilage and are of a rubber-like consistency, fill the gap between the femur and the tibia. These menisci move with the joint surfaces and thus spread the load transmitted through the joint over a larger area than the common area of bone which would otherwise be in contact, irrespective of the degree of flexion.

Figure 1B:
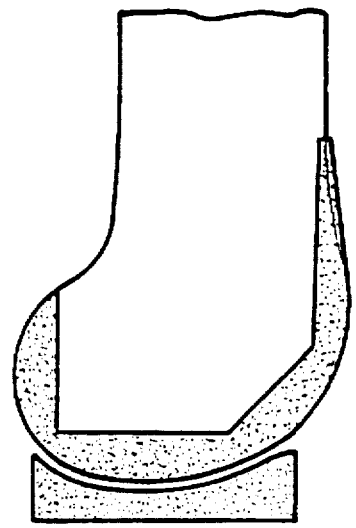
Figure 1C:
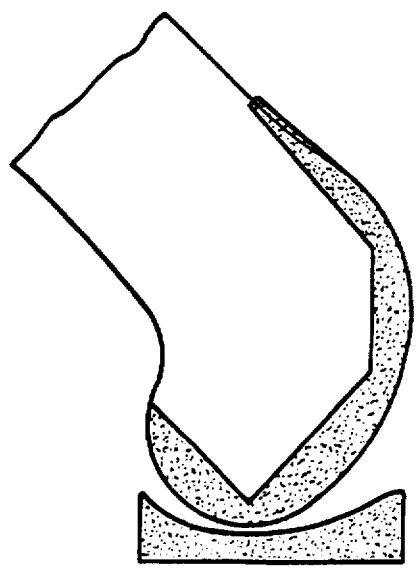
Figure 1D:
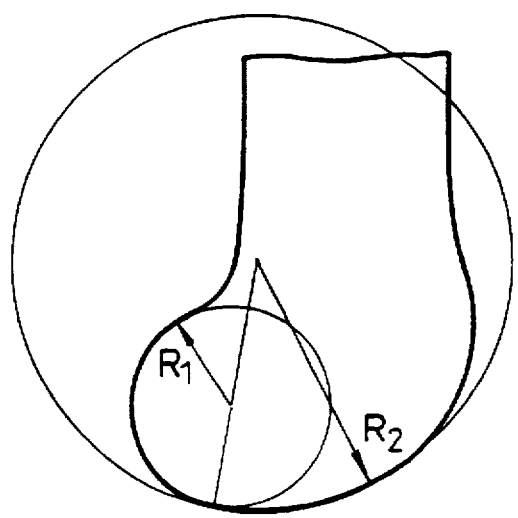

The designer of a knee prosthesis has been faced with a fundamental dilemma. While it is desirable that the femoral prosthesis should have a shape which is close to the anatomical shape, conformity of such a joint throughout flexion is not possible. This is illustrated in FIGS. 1(b) and 1(c). In FIG. 1(b), the joint is shown in extension and in this position, close conformity is quite easy to achieve. However, on flexion as shown in FIG. 1(c), conformity is lost and this results in high contact stresses on the tibial component which greatly increases wear and deformation of the surfaces in contact. In FIG. 1(d), the sagittal profile of the femur is represented and as can be seen, this can be represented with fairly good accuracy by a circular arc distally and a circular arc posteriorly. As shown, the posterior radius $R_1$ is about one half of that the distal radius $R_2$.

Figure 2B:
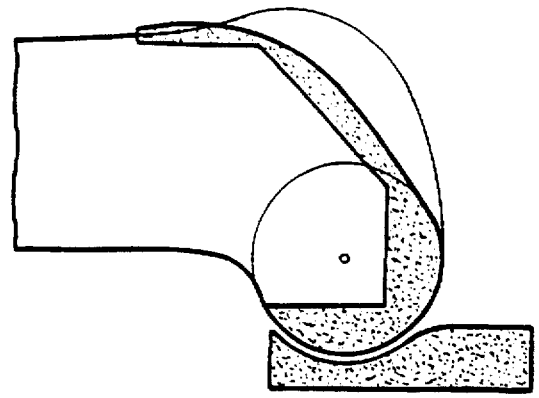
Figure 2C:
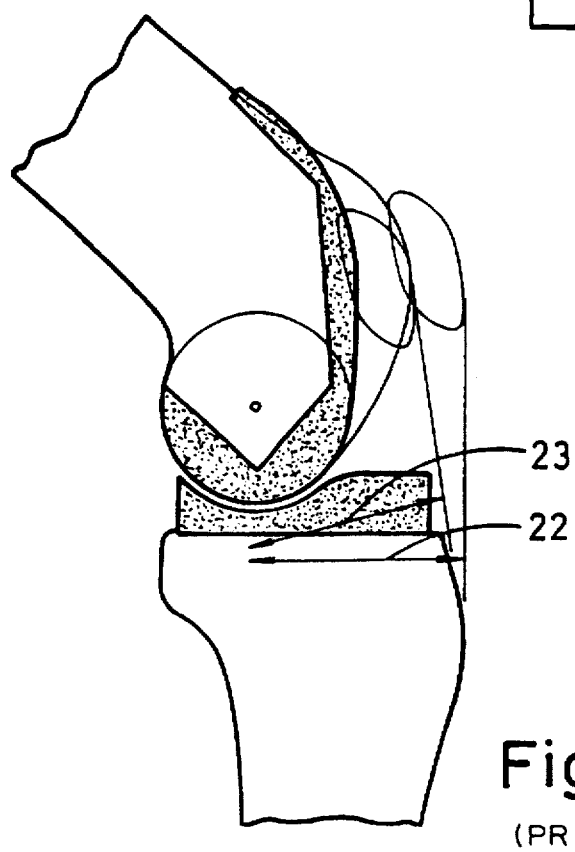

Referring to FIG. 2, this shows one attempt to solve the problem of achieving better conformity between the femoral and tibial components. As shown in FIG. 2(a), the distal end (21) of the femoral condyles has been cut away to provide a constant radius of curvature $R_1$ distally and posteriorly of the femoral component. As shown in FIGS. 2(b) and 2(c), this allows for complete conformity between the femoral component and the tibial component throughout all angles of flexion. However, this solution gives rise to four significant disadvantages. First, all the shear forces and torque forces will be transmitted between the two components and to the component/bone interfaces. Secondly, the freedom of motion, which is required for normal functions, and for the balancing of ligament tensions, will not be allowed to occur. Thirdly, excessive bone resection is required on the distal anterior aspect of the femur. Fourthly, the lever arm of the patella is reduced to a shortened distance (23) in the mid-range of flexion and this is illustrated in FIG. 2(c), compared with the normal lever arm (22).

One embodiment of a prosthesis in accordance with the invention is shown diagrammatically in FIGS. 3(a), 3(b), 3(c) and 3(d), in which 3(a) is a perspective view of the femoral component, 3(b) is a perspective view of the corresponding meniscal component and FIGS. 3(c) and 3(d) are respectively side (sagittal) and front (anterior) views showing the ways in which the femoral and tibial components interact. FIGS. 3(a) and 3(b) show the femoral and meniscal components separated, as does FIG. 3(d).

Referring to FIG. 3(a), it will be seen that the femoral component 41 is a one-piece construction in that the condyles 46 are formed integrally with the patella bearing surface 44. The condyles 46 of the femoral component have a radius $R_3$ which substantially corresponds to the radius $R_4$ of the tibial bearing surfaces 47 of the meniscal component 42. The radius $R_3$ is continued anteriorly, as shown, so as to cut away material in the condylar regions at 43, while leaving the patella bearing surface 44 unaffected. The central region 45 of the meniscal component 42 is shallower than the tibial surfaces 47 to provide clearance for the patella surface anteriorly and to prevent impingement in further flexion posteriorly. Because the patella bearing surface 44 is unaffected by the cutting away of the condylar surfaces anteriorly at 43, the lever arm of the patella is not shortened as in the case of the prior art arrangement shown in FIG. 2. Because of the close conformity between the condylar portions and the corresponding tibial surfaces of the meniscal component, there is uniform spreading of the load transmitted through the femoral components over a large surface of the meniscal component and without loss of the patella lever arm. The cut out regions of the condylar parts of the femoral component do not require additional resection, since they are cut away only in the material of the prosthesis. The required laxity in the joint is provided by mounting the meniscal component 42 for sliding movement on a base plate 72 (see FIG. 7), the base plate being attached in conventional manner, e.g. by a post 74 and locating pins 76 to the resected tibia 46. It will be appreciated that material can be removed by machining a workpiece to form the 'cut-away' parts of the femoral condyles or alternatively the desired 'cut-away' profile can be formed by a process not involving machining, e.g. forging, moulding or casting.

FIGS. 4(a), 4(b) and 4(c) show additional views of the prosthesis shown in FIGS. 3(a) to 3(d), but in more detail. In the anterior view shown in FIG. 4(a), the lateral and medial notches 43 can be seen in the condyles 46. As seen clearly in FIG. 4(a), the condyles are formed with bearing surfaces 51 which are curved in the lateral-medial plane, the bearing surfaces 51 being separated by a track 52 for the patella 54 (see FIG. 4(c)). The sagittal profile of the artificial patella 54 is shown in dotted lines in FIG. 6. As can be seen, instead of having a continuous convex shape in sagittal view it has a flattened inner face 61 and outwardly extending surfaces 55 (FIG. 4(c)), giving greater conformity with the sides of the patella groove. Such increase in conformity leads to greatly reduced contact stresses.

The patella groove or track 52 need not be symmetrically located on the femoral component. Indeed, preferably, it is shifted or widened towards the lateral side 58. The patella forces are higher on the lateral side owing to the geometry of the knee. Widening or shifting the patella track laterally prevents overhang of the plastic or natural patella over the ridge defining the lateral edge of the track, which could cause undesirable wear or inflammation. Because widening of the track has the effect of reducing the available bearing area between the condyles and the corresponding tibial bearing surfaces, widening of the track medially as well would be generally undesirable. Fortunately, the natural knee joint loading forces are considerably lower on the lateral side compared with the medial side. Therefore, shifting the patella track laterally is a good compromise.

A sagittal view of the prosthesis is shown in FIG. 4(b). The surface 44 onto which the patella bears extends in the posterior direction between the notches 43. The condylar tips extend from the notches 43 to terminal superior regions 70. In FIG. 4(b), the curvature of the condyles over the whole bearing surface from the region 70 to the notch 43 has a substantially uniform sagittal radius R. However, this radius can vary to a limited extent for different segments. The segments are defined as A-B, B-C and C-D in FIG. 4(b). By way of example, the radius of the segment A-B for a sagittal plane passing through the line X-Y of FIG. 4(c) may be 19 mm and the corresponding radii B-C and C-D may both be about 22 mms into the lateral and medial notches, the trough of which is designated D. By making the radius of the segment A-B slightly smaller or at least slightly smaller towards the tip 70, there is no tendency for the superior tip 70 to impinge or dig into the tibial surfaces of the meniscal component at maximum flexion.

FIGS. 3(a) to 3(d) show the meniscal component 42 drawn rectangular for simplicity. In practice, the meniscal component has a generally oval or kidney shape as seen in plan. Also, the perspective view of the meniscal component in FIG. 3(b) is slightly misleading in suggesting that the tibial bearing surfaces 47 are separated from the shallower intermediate surface 45 throughout the entire distance from anterior to posterior. At the anterior region 80, the tibial surfaces 47 are separated from the intermediate area 45 by upstanding walls or discontinuities 81. However, this is not necessarily the case in the posterior region 82. In the posterior region, it is preferred that the intermediate portion 45 merges smoothly into the tibial bearing surfaces. This gives better support during flexion and is illustrated in FIGS. 5 and 7. In FIG. 5, which is a lateral-medial section through the meniscal component and tibial base plate, along a line which approximately corresponds with the point C in FIG. 3(b) and is at the deepest point in tibial surfaces 47, it can be seen that the tibial surfaces 47 merge smoothly into the intermediate region 45. The contours of the bearing surfaces of the meniscal component over the entire area in which it cooperates with the femoral component is shown in FIG. 5. FIG. 5 is a perspective view of the meniscal component as seen from the anterior side and shows the intermediate region 45 as being shallower than the tibial surfaces 47, anteriorly to permit the patella bearing surface 44 to pivot from 0° to full flexion without impinging on the region 45. As the tibial surface 47 extends posteriorly, it merges into an area where the curvature is smooth and devoid of any discontinuities in the posterior and lateral-medial directions.

FIG. 7 also shows the meniscal component 42 supported on a tibial base plate 72. The tibial base plate 72 carries a post 74 for attachment to a resected tibia 46 (see FIG. 4(c)), and stabilizing projections 76. The femoral component 41 is attached to a resected femur by locating pegs 82 and by bone cement. The meniscal component is mounted on the tibial base plate so as to be rotational within limits in the plane of the base plate. The tibial base plate and meniscal component are preferably constructed in the manner described in European Patent Application No. 92300878.3 (Publication No. 0498586), the disclosure of which is incorporated herein. Preferably, the tibial base plate carries an upstanding post or rail which engages in a slot 84 (see FIG. 5) in the under surface of the meniscal component.

The meniscal component 42 is guided for movement anteriorly and posteriorly of the tibial component and to provide a degree of rotational freedom of movement as mentioned above. Other references describing methods of guiding meniscal components on tibial base plates include U.S. Pat. No. 4,340,978 and UK Patent No. 2219942.

We claim:

1. A knee prosthesis comprising:

a one part bicondylar femoral component;

a tibial component; and at least one meniscal component interposed between the femoral and tibial components, said meniscal component including slide means for slidingly supporting said meniscus component on said tibial component and for guiding said meniscal component for anterior-posterior sliding movement with respect to said tibial component; and means for permitting relative pivoting movement of the femoral component in the meniscal component throughout a normal range of flexion, said femoral component comprising condylar surfaces separated by a patella bearing surface of defined width which is shaped in a sagittal plane so as to provide in use a normal patella lever arm corresponding in a natural knee to the distance between a center of tibial/ femoral contact pressure and a line extending through the patella, each condylar surface being shaped for substantial conformity with a corresponding tibial bearing surface on a meniscal component through said normal range of flexion, each said condylar surface including a portion being recessed anteriorly thereby providing a recess in each said condylar surface, the recesses being separated by a patella bearing surface, and the meniscal component having projecting portions, each projecting portion providing a contact surface corresponding with a respective said recess when the prosthesis is in extension, thus facilitating said substantial conformity and reduced contact stresses throughout said normal range of flexion without shortening said patella lever arm.

2. A prosthesis comprising:

a one part bicondylar femoral component;

a tibial component; and at least one meniscal component interposed between the femoral and tibial components and guided for anterior-posterior sliding movement on said tibial component, and permitting relative pivoting movement of the femoral component in the meniscal component throughout a normal range of flexion, said femoral component comprising condylar surfaces separated by a patella bearing surface of defined width which is shaped in a sagittal plane so as to provide in use a normal patella lever arm corresponding in a natural knee to the distance between a center of tibial/femoral contact pressure and a line extending through the patella, each condylar surface being shaped for substantial conformity with a corresponding tibial bearing surface on a meniscal component through said normal range of flexion, each said condylar surface including a portion being recessed anteriorly thereby providing a recess in each said condylar surface, the recesses being separated by a patella bearing surface, and the meniscal component having projecting portions, each projecting portion providing a contact surface corresponding with a respective said recess when the prosthesis is in extension, thus facilitating said substantial conformity and reduced contact stresses throughout said normal range of flexion without shortening said patella lever arm, wherein the meniscal component is rotatably mounted on the tibial component so as to permit a degree of rotational movement of the meniscal component on the tibial component.

3. A prosthesis as claimed in claim 1 wherein the meniscal component has an intermediate region between said projecting portions, the intermediate region being shaped to provide clearance for the patella bearing surface of the femoral component in flexion.

4. A prosthesis as claimed in claim 1 wherein the patella bearing surface forms a track when said prosthesis is viewed anteriorly, the track being shifted laterally of a center of said femoral component so as to prevent patella overhanging a lateral edge of the track.

5. A prosthesis as claimed in claim 1 wherein the meniscal component is shaped anteriorly to provide an intermediate surface between said projecting portions which is recessed from said tibial bearing surfaces.

6. A prosthesis as claimed in claim 5 wherein the meniscal component is shaped posteriorly so that the tibial bearing surfaces merge into the intermediate surface without any discontinuity.

7. The prosthesis as claimed in claim 1 wherein width of said patella bearing surface forms a track when said prosthesis is viewed anteriorly which is sized so as to prevent a patella overhanging a lateral edge of the patella bearing surface.

* * * * *